(12) United States Patent
Batchelor et al.

(10) Patent No.: US 11,523,860 B2
(45) Date of Patent: *Dec. 13, 2022

(54) ELECTROSURGICAL DEVICE FOR VESSEL SEALING AND CUTTING (71) Applicant: GYRUS ACMI, INC., Southborough, MA (US)

(72) Inventors: Kester J. Batchelor, Mound, MN (US); Huisun Wang, Maple Grove, MN (US)

(73) Assignee: Gyrus ACMI, Inc., Westborough, MA (US)

(*) Notice: Subject to any disclaimer, the term of this patent is extended or adjusted under 35 U.S.C. 154(b) by 536 days.

This patent is subject to a terminal disclaimer.

(21) Appl. No.: 16/534,047

(22) Filed: Aug. 7, 2019

(65) Prior Publication Data
US 2021/0038287 A1 Feb. 11, 2021

Related U.S. Application Data (63) Continuation of application No. 16/068,753, filed as application No. PCT/US2017/012504 on Jan. 6, (Continued)

(51) Int. Cl.
A61B 18/14 (2006.01)
A61B 18/00 (2006.01)

(52) U.S. Cl.
CPC .. *A61B 18/1442* (2013.01); *A61B 2018/0063* (2013.01); *A61B 2018/00589* (2013.01);
(Continued)

(58) Field of Classification Search
CPC .............. A61B 18/1442; A61B 18/085; A61B 18/1445; A61B 2018/00589;
(Continued)

(56) References Cited

U.S. PATENT DOCUMENTS 5,269,780 A 12/1993 Roos
5,445,638 A 8/1995 Rydell et al.
(Continued)

FOREIGN PATENT DOCUMENTS

EP 1287788 A1 3/2003
EP 1330991 A1 7/2003
(Continued)

OTHER PUBLICATIONS

"U.S. Appl. No. 15/781,735, Non Final Office Action dated Sep. 3, 2020", 19 pgs.
(Continued)

*Primary Examiner* — Thomas A Giuliani
(74) *Attorney, Agent, or Firm* — Schwegman Lundberg & Woessner, P.A.

(57) ABSTRACT

An electrosurgical medical device that includes a jaw assembly. The jaw assembly includes a first jaw body and a cutting member; and a second jaw body. During a first use state, the medical device is configured to pass a therapy current supplied by a power source between the first jaw body and the second jaw body to electrosurgically effect an anatomical feature. During a second use state, an anatomical feature is electrosurgically effected by contacting the anatomical feature with a medial edge of the cutting member while a second therapy current from the power source is passed between the cutting member and the first jaw body and/or the second jaw body.

20 Claims, 4 Drawing Sheets

Related U.S. Application Data 2017, now Pat. No. 10,413,350, which is a continuation-in-part of application No. PCT/US2016/012823, filed on Jan. 11, 2016.

(60) Provisional application No. 62/317,855, filed on Apr. 4, 2016.

(52) U.S. Cl.
CPC .............. *A61B 2018/00601* (2013.01); *A61B 2018/1452* (2013.01); *A61B 2018/1462* (2013.01)

(58) Field of Classification Search
CPC .. A61B 2018/00601; A61B 2018/0063; A61B 2018/1452; A61B 2018/1412; A61B 2018/00607; A61B 2018/126; A61B 2018/1455
USPC ............................... 606/41, 50–52, 205, 207
See application file for complete search history.

(56) References Cited

U.S. PATENT DOCUMENTS

| | | | |
|---|---|---|---|
| 5,458,598 A | 10/1995 | Feinberg et al. | |
| 5,735,849 A | 4/1998 | Baden et al. | |
| 5,766,166 A | 6/1998 | Hooven | |
| 5,908,420 A * | 6/1999 | Parins ................ | A61B 18/1445 |
| | | | 606/174 |
| 5,951,549 A | 9/1999 | Richardson et al. | |
| 5,951,551 A | 9/1999 | Erlich | |
| 6,086,586 A | 7/2000 | Hooven | |
| 6,113,596 A | 9/2000 | Hooven et al. | |
| 6,152,923 A | 11/2000 | Ryan | |
| 6,190,386 B1 | 2/2001 | Rydell | |
| 6,270,497 B1 | 8/2001 | Sekino et al. | |
| 6,273,887 B1 | 8/2001 | Yamauchi et al. | |
| 6,334,860 B1 | 1/2002 | Dorn | |
| 6,447,511 B1 | 9/2002 | Slater | |
| 6,676,660 B2 | 1/2004 | Wampler et al. | |
| 6,679,882 B1 | 1/2004 | Kornerup | |
| 6,929,641 B2 | 8/2005 | Goble et al. | |
| 6,966,907 B2 | 11/2005 | Goble | |
| 6,984,231 B2 | 1/2006 | Goble et al. | |
| 7,147,637 B2 | 12/2006 | Goble | |
| 7,204,835 B2 | 4/2007 | Latterell et al. | |
| 7,208,005 B2 * | 4/2007 | Frecker .................. | A61B 17/29 |
| | | | 606/205 |
| 7,232,440 B2 | 6/2007 | Dumbauld et al. | |
| 7,442,194 B2 | 10/2008 | Dumbauld et al. | |
| 8,257,352 B2 | 9/2012 | Lawes et al. | |
| 8,262,655 B2 | 9/2012 | Ghabrial et al. | |
| 8,273,085 B2 | 9/2012 | Park et al. | |
| 8,597,296 B2 | 12/2013 | Lawes et al. | |
| 10,413,350 B2 * | 9/2019 | Batchelor .......... | A61B 18/1445 |
| 2002/0188294 A1 | 12/2002 | Couture et al. | |
| 2003/0073990 A1 | 4/2003 | Goble et al. | |
| 2003/0109876 A1 | 6/2003 | Yamauchi et al. | |
| 2003/0163123 A1 | 8/2003 | Goble et al. | |
| 2004/0122423 A1 | 6/2004 | Dycus et al. | |
| 2005/0113826 A1 | 5/2005 | Johnson et al. | |
| 2006/0020265 A1 | 1/2006 | Ryan | |
| 2006/0084973 A1 | 4/2006 | Hushka | |
| 2006/0224158 A1 | 10/2006 | Odom et al. | |
| 2006/0271038 A1* | 11/2006 | Johnson ........... | A61B 17/07207 |
| | | | 606/49 |
| 2008/0015575 A1 | 1/2008 | Odom et al. | |
| 2008/0045947 A1 | 2/2008 | Johnson et al. | |
| 2010/0036371 A1 | 2/2010 | Park et al. | |
| 2011/0046623 A1 | 2/2011 | Reschke | |
| 2011/0319886 A1 | 12/2011 | Chojin et al. | |
| 2012/0323238 A1 | 12/2012 | Tyrrell et al. | |
| 2013/0018411 A1 | 1/2013 | Collings et al. | |
| 2013/0123837 A1 | 5/2013 | Roy et al. | |
| 2014/0100568 A1 | 4/2014 | Garrison | |
| 2014/0276794 A1 | 9/2014 | Batchelor et al. | |
| 2014/0288541 A1 | 9/2014 | Eshkol et al. | |
| 2014/0288553 A1 | 9/2014 | Johnson et al. | |
| 2015/0088128 A1 | 3/2015 | Couture | |
| 2015/0137422 A1 | 5/2015 | Horner et al. | |
| 2016/0346035 A1 | 12/2016 | Takei et al. | |
| 2018/0360525 A1 | 12/2018 | Batchelor et al. | |
| 2019/0021785 A1 | 1/2019 | Batchelor et al. | |

FOREIGN PATENT DOCUMENTS

| | | |
|---|---|---|
| EP | 3386408 A1 | 10/2018 |
| EP | 3389533 A1 | 10/2018 |
| EP | 3389533 B1 | 10/2019 |
| EP | 3603555 A1 | 2/2020 |
| WO | 2004/032777 A1 | 4/2004 |
| WO | WO-2015047611 A1 | 4/2015 |
| WO | WO-2017123189 A1 | 7/2017 |
| WO | WO-2017123468 A1 | 7/2017 |

OTHER PUBLICATIONS

"U.S. Appl. No. 15/781,735, Response filed Dec. 3, 2020 to Non Final Office Action dated Sep. 3, 2020", 21 pgs.

"European Application Serial No. 19191726.9, Extended European Search Report dated Jan. 7, 2020", 7 pgs.

"European Application Serial No. 19191726.9, Response filed Aug. 5, 2020 to Extended European Search Report dated Jan. 7, 2020", 9 pgs.

"U.S. Appl. No. 15/781,735, Preliminary Amendment filed Jun. 6, 2018", 7 pgs.

"U.S. Appl. No. 16/068,753, Non Final Office Action dated Feb. 15, 2019", 14 pgs.

"U.S. Appl. No. 16/068,753, Notice of Allowance dated May 22, 2019", 12 pgs.

"U.S. Appl. No. 16/068,753, Preliminary Amendment filed Jul. 9, 2018", 6 pgs.

"U.S. Appl. No. 16/068,753, Response filed May 8, 2019 to Non Final Office Action dated Feb. 15, 2019", 14 pgs.

"European Application Serial No. 17701938.7, Communication Pursuant to Article 94(3) EPC dated Jan. 24, 2019", 4 pgs.

"European Application Serial No. 17701938.7, Intention to Grant dated Jul. 8, 2019", 33 pgs.

"European Application Serial No. 17701938.7, Response filed Apr. 10, 2019 to Communication Pursuant to Article 94(3) EPC dated Jan. 24, 2019", 30 pgs.

"European Application Serial No. 19191726.9, Extended European Search Report dated Jan. 7, 2020", 8 pgs.

"International Application Serial No. PCT/US2016/012823, International Preliminary Report on Patentability dated Jul. 26, 2018", 18 pgs.

"International Application Serial No. PCT/US2016/012823, International Search Report dated Nov. 7, 2016", 5 pgs.

"International Application Serial No. PCT/US2016/012823, Written Opinion dated Nov. 7, 2016", 16 pgs.

"International Application Serial No. PCT/US2017/012504, International Preliminary Report on Patentability dated Jul. 26, 2018", 16 pgs.

Search Report and Written Opinion for International Application No. PCT/US2017/012504; dated May 18, 2017.

"U.S. Appl. No. 15/781,735, Examiner Interview Summary dated Nov. 1, 2021", 2 pgs.

"U.S. Appl. No. 15/781,735, Final Office Action dated Mar. 23, 2021", 18 pgs.

"U.S. Appl. No. 15/781,735, Response filed Jun. 23, 2021 to Final Office Action dated Mar. 23, 2021", 19 pgs.

"U.S. Appl. No. 15/781,735, Supplemental Amendment and Resonse filed Dec. 15, 2021 to Final Office Action received Mar. 23, 2021", 20 pgs.

"European Application Serial No. 16705329.7, Communication pursuant to Rule 164(2) EPC dated Dec. 10, 2021", 7 pgs.

(56) References Cited

OTHER PUBLICATIONS

"U.S. Appl. No. 15/781,735, Response filed Jun. 2, 2022 to Non Final Office Action dated Mar. 2, 2022", 16 pgs.
"European Application Serial No. 16705329.7, Notification Regarding Rule 164 and Article 94(3) EPC dated Apr. 7, 2022", 13 pgs.
"U.S. Appl. No. 15/781,735, Non Final Office Action dated Mar. 2, 2022", 20 pgs.

* cited by examiner

ELECTROSURGICAL DEVICE FOR VESSEL SEALING AND CUTTING

CROSS-REFERENCE TO RELATED APPLICATIONS

This application is a Continuation of U.S. patent application Ser. No. 16/068,753 filed Jul. 9, 2018 and issued as U.S. Pat. No. 10,413,350; which is a National Stage Application of PCT/US2017/012504, filed Jan. 6, 2017, which is a Continuation-in-Part of PCT/US2016/012823 filed Jan. 11, 2016, which claims the benefit of U.S. Provisional Patent Application Ser. No. 63/317,855, filed Apr. 4, 2016; the contents of which are incorporated by reference in their entireties.

FIELD

These teachings relate to an electrosurgical device for vessel sealing and cutting.

BACKGROUND

Forceps are plier-like instruments that have opposing jaws. The jaws can be used during a medical procedure to effect an anatomical feature, such as a vessel or tissue. For example, a vessel or tissue can be positioned between the opposing jaws, and the jaws can be used to move, grip, grasp, push, pull, cut, dissect and/or otherwise effect the vessel or tissue.

Some forceps, such as those disclosed in U.S. Pat. Nos. 5,735,849, 5,445,638, 6,190,386, 6,113,596, and 6,679,882, which are hereby incorporated by reference herein for all purposes, include electrosurgical capabilities for electrically effecting an anatomical feature. For example, a vessel or tissue can be positioned between the opposing jaws, and a therapy current supplied by a power source can be passed between the jaws to seal or coagulate the vessel or tissue. Afterwards, a mechanical cut blade can be advanced through the sealed or coagulated vessel or tissue to cut the vessel or tissue.

While suitable for the intended purpose, utilizing a mechanical cut blade to cut a vessel or tissue after sealing requires additional mechanisms to advance and retract the cut blade, which may undesirably add cost, weight, and complexity to the forceps. Also, additional packaging space may be required between the opposing jaws and/or in the hand piece of the forceps to house the cut blade and the mechanisms required for moving the cut blade, which may undesirably increase the size and weight of the forceps.

Improvement in the art may be desired. For example, it may be desirable to have an improved electrosurgical device for vessel sealing and cutting.

SUMMARY

These teachings provide an improved vessel sealing and cutting device. These teachings provide a medical device that can be used to coagulate or seal an anatomical feature and then cut or separate the sealed or coagulated anatomical feature with an edge of an energized cutting member that is contained within the jaw assembly. The sealed anatomical feature may be cut with an inside or medial edge of the cutting member. Advantageously, by utilizing the teachings according to this disclosure, a user can seal and cut an anatomical feature with two steps: 1) clamp and coagulate the anatomical feature in the jaw assembly; and 2) sheer and cut the anatomical feature between the jaw assembly with an edge of an energized cutting member. The edge preferably extends towards a center region of the jaw assembly.

These teachings also provide an electrosurgical medical device that includes a jaw assembly. The jaw assembly includes a first jaw body and a cutting member; and a second jaw body. During a first use state, the medical device is configured to pass a therapy current supplied by a power source between the first jaw body and the second jaw body to electrosurgically effect an anatomical feature. During a second use state, an anatomical feature is electrosurgically effected by contacting the anatomical feature with a medial edge of the cutting member while a second therapy current from the power source is passed between the cutting member and the first jaw body and/or the second jaw body.

These teachings further provide an electrosurgical medical device that includes a jaw assembly. The jaw assembly includes a first jaw comprising a first jaw body and a cutting member; and a second jaw comprising a second jaw body including an anvil. The medical device is operable in a first use state and in a second use state. D during the first use state, the anatomical feature is positioned between the first jaw body and the second jaw body, and the first jaw body and/or the second jaw body are vertically moveable along a first path relative to each other to clamp the anatomical feature between the cutting member and the second jaw body in the first use state. During the second use stale the anatomical feature is positioned between the cutting member and the anvil and the first jaw body and/or the second jaw body are moveable along a second path relative to each other to cut the anatomical feature with an interior edge of the cutting member in the second use state. The first path is different from the second path.

Further yet, these teachings provide an electrosurgical medical device that includes a jaw assembly. The jaw assembly includes a first jaw body and a cutting member; and a second jaw body and an anvil. During the first use state, a gap is defined between an interior edge of the cutting member and the anvil. During a second use state the gap is taken up and the medical device is configured to pass a second use state therapy current from the cutting member through the anatomical feature to electrosurgically effect the anatomical feature in the second use state.

These teachings also provide a method of surgically effecting an anatomical feature. The method includes positioning an anatomical feature between a first jaw body and a second jaw body of a medical device. The method includes clamping the anatomical feature between a cutting member located on the first jaw body and the second jaw body. The method includes surgically effecting the anatomical feature between the cutting member and the second jaw body during a first use state. The method includes repositioning the first jaw body and/or the second jaw body. The method includes electrosurgically effecting the anatomical feature with a medial edge of the cutting member during a second use state.

These teachings also provide a jaw assembly of a forceps. The jaw assembly comprising a first jaw body and a second jaw body. The first jaw body having an effecting surface and a medial edge disposed longitudinally on the sealing surface. The second jaw body having an effecting surface and a second effecting surface. The second effecting surface being stepped off from the first effecting surface. The second jaw body also having a medial edge that is located between the first effecting surface and the second effecting surface. The first jaw body and the second jaw body are disposed in opposition relative to one another, and at least one of the jaw bodies is movable relative to the other jaw body between an open position and a closed position for the jaw bodies to grasp tissue therebetween. In both the closed position and the open position, the medial edge of the first jaw body is in opposition to the medial edge of the second jaw body.

These teachings also provide forceps comprising: a jaw assembly comprising a first jaw body, a second jaw body, and a medial edge. The first jaw body having an electrically conductive effecting surface configured to connect to a source of electrosurgical energy. The second jaw body having an electrically conductive effecting surface configured to connect to the source of electrosurgical energy. The medial edge is disposed longitudinally on the sealing surface of the first jaw body or the second jaw body. The medial being in an offset relation to the effecting surface of the other jaw body. The first jaw body and the second jaw body are disposed in opposition relation relative to one another, and at least one of the jaw bodies is movable relative to the other jaw body between an open position and a closed position for the jaw bodies to grasp tissue therebetween.

These teachings also provide a method of using forceps, the method comprising grasping tissue between a first jaw body and a second jaw body of the forceps. The first jaw body having an effecting surface and a medial edge disposed longitudinally on the effecting surface. The second jaw body have a first effecting surface, a second effecting surface, and a medial edge between the first effecting surface and the second effecting surface. The second effecting surface being stepped off from the first effecting surface. A position of the medial edge of the first jaw body is in opposition to the medial edge of the second jaw body surface. The method including laterally moving the first jaw body or the second jaw body to cut tissue between the jaw bodies.

DETAILED DESCRIPTION

This disclosure claims the benefit of U.S. Provisional Patent Application No. 62/317,855 filed on Apr. 4, 2016 and International Application Number PCT/US16/12823 filed on Jan. 11, 2016, the disclosures of which are both hereby incorporated by reference herein in their entireties for all purposes.

Medical Device. The present teachings provide a medical device. The medical device can be any device for effecting an object or anatomical feature. Effecting may mean, for example, compressing, thinning, manipulating, engaging, moving, grasping, gripping, constricting, pushing, pulling, cutting, tearing, coagulating, sealing, cauterizing, dissecting, fulgurating, the like, or a combination thereof an anatomical feature. The anatomical feature may be any anatomical feature, such as a vessel, tissue, vein, artery, the like, or a combination thereof.

The medical device can be used in virtually any medical procedure. The medical device can be used in open procedures, laparoscopic procedures, or both. The medical device may be any device having jaws, or a jaw assembly. The medical device can be medical forceps, bipolar forceps, bipolar electrosurgical forceps, a bipolar sealing forceps, bipolar cutting forceps, a bipolar sealing forceps and monopolar cutting forceps, or a combination thereof.

Power Source. The medical device may be in communication with one or more power sources. The power source may provide the one or more electrical currents, therapies, and/or signals to the medical devices and/or to the elements of the medical device. The power source may be a generator. The power source may be a source of electrosurgical energy. The power source may be of the type described in U.S. Pat. No. 7,282,048B2 issued Oct. 16, 2007, the teachings of which are hereby incorporated by reference herein for all purposes.

The medical device may be configured to receive one or more electrical currents, therapies, and/or signals provided by the power source that include monopolar energy and/or bipolar energy. The one or more electrical currents, therapies, and/or signals may include a cut waveform and/or a coagulation or sealing waveform. During use, an electrical circuit may be completed by passing monopolar energy or bipolar energy from the power source to the jaw assembly and/or to the one or more elements of the jaw assembly and/or to a remote electrode that is/are in electrical communication with one or more poles of the power source. For example, during use, a cut waveform may be delivered continuously from the power source to the medical device, the jaw assembly, and/or one or more elements of the jaw assembly, and can be described as a higher curren/lower voltage waveform compared to the coagulation waveform. For example, during use, a coagulation waveform may be modulated or interrupted from the power source to the medical device, the jaw assembly, and/or one or more elements of the jaw assembly, and can be described as a lower current/higher voltage waveform compared to the cut waveform.

One or more therapy currents or signals may be passed to the medical device, the jaw assembly, and/or one or more elements of the jaw assembly while the jaw assembly is in a closed position, in an open position, and/or in a position therebetween, or while moving between a closed position and the open position.

Hand piece. The medical device may include a hand piece. The hand piece may function to house, support, and or contain the jaw assembly, and/or one or more elements of the jaw assembly, such as the one or more jaws, jaw bodies, electrodes, cutting members, insulators, anvils, or a combination thereof. The hand piece may include one or more buttons for activating supply of the one or more therapy currents from the power source. The hand piece may include one or more features, like one or more sliders, that may function to lock the arms or the jaw assembly in an open position, in a closed position, or in a position in between. The hand piece may be manipulated to move the jaw assembly between an open position and a closed position.

Jaws. The medical device and/or the jaw assembly may include one or more jaws. The jaws may be configured to surgically effect an anatomical feature. For example, the jaws may be used to capture, grip, grasp, and/or manipulate an anatomical feature; provide a clamping force to secure an anatomical feature; provide retraction of an anatomical feature; provide a compression or gripping force on or across an anatomical feature; or a combination thereof. The jaws may be used in electrosurgery to cut, coagulate, cauterize, dissect, and/or fulgurate an object or anatomical feature (e.g., surgically or electrically cut, coagulate, or effect an anatomical feature). The jaws may be moved or pivot between an open and closed position, and/or a position in between. The one or more jaws may include, or may be referred to herein, as an upper jaw, a lower jaw, a first jaw, a second jaw, opposing jaws, or a combination thereof. Each of the one or more jaws may carry, or may be comprised of, one or more jaw bodies, one or more cutting members, one or more anvils, one or more electrodes, one or more insulators, one or more standoffs, or a combination thereof.

For example, a jaw may comprise an electrode that is stacked on an insulator, and the insulator may be stacked on a jaw. One or both of the electrode and the jaw may be electrically conductive and connected to a common pole or an opposing pole of the power supply.

The jaw assembly may be moveable between an open position and a closed position. The open position may be a steady state position, and the jaw assembly may be moved from the open position to the closed position by manipulating the arms of the band piece. When moving the closed position, one jaw may move towards the other jaw, or both jaws may move towards each other.

The closed position of the jaw assembly may be defined as a position of the jaws where virtually no gap, or only a slight gap, exists between the effecting surfaces or edges, the opposing jaws or jaw bodies, an edge or surface of the cutting member and an edge or surface of the anvil, or a combination thereof. In the closed position, a clamping or gripping force applied on the anatomical feature may be higher or larger than a damping or gripping force applied on the anatomical feature when the jaws are in the open position.

The jaw assembly may have more than one open position and more than one closed position. For example, the jaw assembly can be moved along a first path between an open and closed position, and also along a second path between an open and closed position. When the jaw assembly is in the closed position after moving one or both of the jaws alone a first path, an anatomical feature may be effected by, for example, clamping and/or coagulating the anatomical feature between the jaws. When the jaw assembly is in the closed position after moving the opposing jaws along the second path, an anatomical feature may be effected by, for example, cutting the anatomical feature. To effect an anatomical feature, the jaw assembly may be moved along the first path followed by the second path; moved only along the first path; moved only along the second path; moved along the second path then along the first path; or a combination thereof.

Movement Paths. One or both of the jaws may be moveable along one or more paths. The paths may provide for the jaw assembly to be moved or pivoted between an open and closed position, and/or a position in between. A first path may include one or both of the jaws moving towards and away from one another from an open position to a closed position and from a closed position to an open position. For example, the first path may include the first jaw moving towards the second jaw and/or the second jaw moving towards the first jaw. The first path may be generally linear or generally non-linear. Relative to a center axis of the jaw assembly, for example the axis 36 illustrated at FIG. 2, the first path may be generally along or generally parallel to the center axis of the jaw assembly. That is, the first path may be generally vertical as illustrated by the arrows in FIG. 2. However, the first path may also be arcuate, canted, or skewed relative to the center axis 36.

A second path may include one or both of the jaws moving towards and away from one another from an open position to a closed position and from a closed position to an open position. For example, the second path may include the first jaw moving towards the second jaw and/or the second jaw moving towards the first jaw. The second path may be generally linear or generally non-linear. Relative to a center axis of the jaw assembly, for example the axis 36 illustrated at FIG. 2, the second path may be generally orthogonal the center axis of the jaw assembly. That is, the second path may be generally horizontal or generally perpendicular to the axis 36 as illustrated by the arrows in FIG. 2. However, second first path may be canted, arcuate, or skewed relative to the center axis 36. The first path and the second path may thus be different.

Jaw Bodies. One or more of the jaw bodies, sealing plates, or both may be at least partially constructed from a conductive material. One or more of the jaw bodies, sealing plates, or both may be at least partially constructed from or covered by an insulator. For example, one or more of the jaw bodies, sealing plates, or both may have an outer or upper surface and/or side surfaces that are at least partially constructed from or covered by an insulator. As used herein, the outer or upper surface may oppose an effecting surface and/or may be a surface that is not used to effect an anatomical feature. One or both of the jaw bodies may be constructed from a bulk conductive material. One or more of the jaw bodies may be in electrical communication with one or more poles of the power source. Preferably, the opposing jaw bodies are not in electrical communication with the same pole of the power supply. Instead, preferably, the opposing jaw bodies are in electrical communication with opposing poles of the power source.

Figure 6:
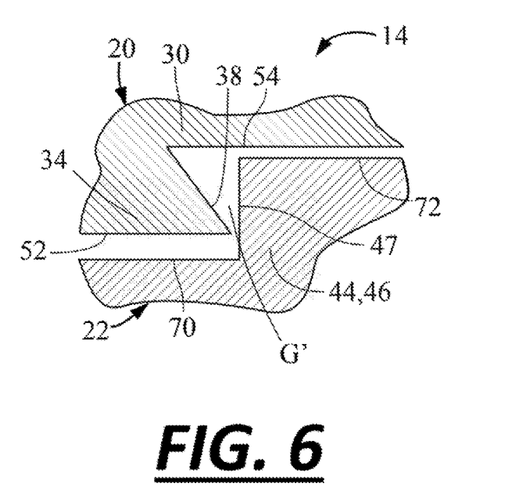
FIG. 6 is a cross-sectional view of the jaw assembly.

Cutting Member. The cutting member may function to cut an anatomical feature. The cutting member be an edge or effecting surface of a sealing plate or an edge or effecting surface jaw body. That is, referring to FIG. 2, for example, the cutting member may be an inner or lateral edge 38 of a sealing plate 34. Referring to FIG. 6, for example, the cutting member may be an inner or lateral edge 38 of the first jaw body 30.

The cutting member may be fabricated from a suitable material such as sheet metal. The cutting member may be a plate that is flat and has constant thickness or the thickness may vary. The cutting member may have a mass that is less than the mass of one or more of the jaw bodies so that the cutting member heats more than the one or more jaw bodies with more mass so that, during a particular use state when connected to the power source, the cutting member becomes the active electrode rather than a return electrode. The cutting member may have a specific heat that is less than the specific heat of one of more of the jaw bodies so that the one or more jaw bodies heat less than the cutting member so that during a particular use state the cutting member may become the active electrode rather than a return electrode. The cutting member may have a thermal conductivity that: is less than the thermal conductivity of one of more of the jaw bodies so that the cutting member becomes the active electrode rather than a return electrode.

The cutting member may be a separate and discrete element that is fixed to the first jaw body or the second jaw body, for example, FIGS. 2-5. An insulator may be disposed between the discrete cutting member and jaw body. Alternatively, the cutting member may be made integral with a jaw body, for example FIGS. 6-9.

Anvil. The anvil may function provide a surface against which an anatomical feature can be effected or cut. The anvil may be a surface, edge, or element that generally opposes the cutting member. The anvil may be an insulator. The anvil may be a conductor. The anvil may be a discrete component connected to attached to a jaw body, or the anvil may be an integral surface or edge of a jaw body. The anvil may be a standoff that prevents the opposing jaws or cutting member from contacting one another thus preventing arcing or an electrical short. The anvil may have a top face that faces an opposing jaw body. Relative to a center axis, the anvil may have an inner or medial edge that opposes or faces an inner or medial edge of a cutting member. A lateral edge of the anvil may be laterally fluid with the jaw body on which it is carried.

Effecting surfaces or edges. The one or more jaws, jaw bodies, electrodes, cutting members, anvils or a combination thereof may include one or more effecting surfaces or edges. The one or more effecting surfaces or edges may function to contact an anatomical feature to effect the anatomical feature during a particular use state. For example, these effecting surfaces or edges may be one or more of the surfaces or edges identified in the figures at least at reference numerals 32, 38, 47, 52, 54, 70, 72, and/or 74. One or more of these effecting surfaces or edges may be sealing surfaces or edges and/or cutting surfaces or edges. One or more of the effecting surfaces or edges may be at least partially smooth, flat, contoured, serrated, textured, toothed, undulating, wave-shaped, planar, irregular, knurled, grit blasted, angled, rounded, curved, or a combination thereof. One or more of the effecting surfaces or edges may horizontal, vertical, canted, slanted, rounded, angled, or a combination thereof relative to an axis of the jaw assembly or relative to other of these surfaces. One or more of the effecting surfaces or edges may include one or more ridges, teeth, mouse teeth, gaps, openings, of a combination thereof.

One or more of the effecting surfaces or edges may be insulators. One or more of the effecting surfaces or edges may be at least partially conductive and used in electrosurgery to electrically effect an anatomical feature.

Insulators. The one or more jaws, jaw bodies, cutting members, electrodes, effecting surfaces or edges, or a combination thereof may include one or more insulators. The insulator may function to insulate, restrict, and/or prevent electricity, current, and or therapy signals from passing between elements of the jaw assembly (i.e., between a cutting member and a jaw body, for example). The insulator may function to prevent the jaw assembly, the one or more jaw bodies, and/or cutting member or the effecting surfaces thereof from arcing during electrosurgery. The insulator may be formed from any suitable material having insulating properties such as, for example, Nylon, PEEK silicon rubber, a ceramic material, or a combination thereof.

Figure 1:
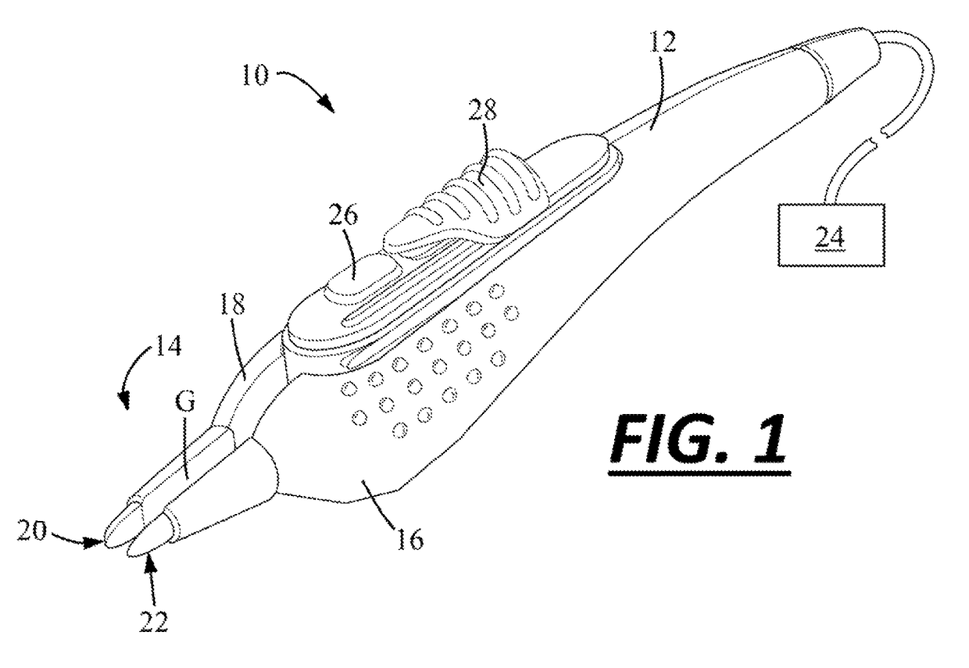
FIG. 1 is a perspective view of a medical device that includes a jaw assembly.

FIG. 1 illustrates the medical device 10. The medical device 10 includes a hand piece 12 and a jaw assembly 14. The hand piece 12 includes a pair of arms 16, 18 that are moveable relative to each other. The jaw assembly 14 comprises a first jaw 20 connected to the first arm 16, and a second jaw 22 connected to the second arm 18.

The arms 16, 18 are biased apart so that a gap 1 is defined between the arms 16, 18 and thus also between the jaws 20, 22. By moving one or both of the arms 16, 18 towards each other, the arms 16, 18 and thus the jaws 20, 22 can be moved from an open position illustrated in FIG. 1 to effect an anatomical feature. The medical instrument 10 includes a slider 28. After the jaw assembly 14 is moved into a closed position, the slider 28 can be moved to lock the arms 16, 18 and thus the jaws 20, 22 together to prevent the arms 16, 18 and the jaws 20, 22 from moving into the open position.

The medical device 10 is in communication with a power source 24. The medical device 10 includes a button 26. When the button 26 is activated, the medical device 10 is configured to received and then pass a therapy current between one or more of the elements of the medical device 10 described further below to electrically effect an anatomical feature.

Figure 2:
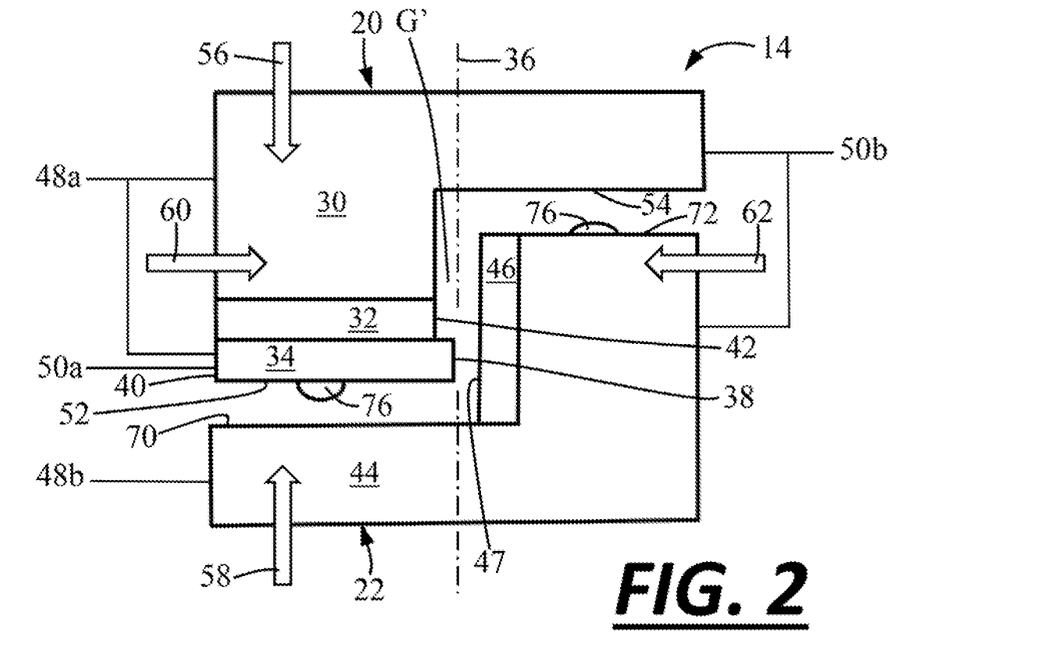
FIG. 2 is a cross-sectional view of the jaw assembly.

FIG. 2 illustrates a cross section of the jaw assembly 14. The jaw assembly 14 includes a first jaw 20 and a second jaw 22. The first jaw 20 includes a fist jaw body 30, an insulator 32 and a cutting member 34. Relative to a center axis 36, the cutting member 34 includes an interior or medial edge 38 and an exterior or lateral edge 40. Relative to the center axis 36, the interior or medial edge 38 of the cutting member 34 extends medially beyond an interior or medial edge 42 of the insulator 32. The second jaw 22 includes a second jaw body 44 that is or includes an anvil 46.

With continued reference to FIG. 2, both the first jaw body 30 and the cutting member 34 are in electrical communication with a first pole 48a of the power source 24 (FIG. 1). The second jaw body 44 is in electrical communication with a second pole 48b of the power source 24. A first therapy current is supplied from the poles 48a, 48b of the power supply 24 to the first jaw body 30, the second jaw body 44, and the cutting member 32.

With continued reference to FIG. 2, the cutting member 34 is also in electrical communication with another first pole 50a of the power source 24 (FIG. 11 The first jaw body 30 and the second jaw body 44 are both in electrical communication with another second pole 50b of the power source 24. A second therapy current is supplied from the poles 50a, 50b of the power supply 24 to the first jaw body 30, the second jaw body 44, and the cutting member 34.

With continued reference to FIG. 2, the medical device 10 is operable or can be used in a first use state. In the first use state, an anatomical feature (not illustrated) is positioned between the first jaw 20 and the second jaw 22. More precisely, the anatomical feature can be positioned and/or clamped between an effecting surface 52 of the cutting member 34 and an opposing effecting surface 70 of the second jaw body 44 and/or between a surface 54 of the first jaw body 30 and the opposing effecting surface 72 of the second jaw body 44. The anatomical feature can be captured, sandwiched, and/or clamped therebetween by moving the first jaw 20 towards the second jaw 22 generally in direction 56, and/or moving the second jaw 22 towards the first jaw 20 generally in direction 58 such that the jaw assembly 14 is moved into a closed position.

The medical device 10 is configured to pass the first therapy current supplied by the poles 48a, 48b of the power source 24 between the first jaw body 30 and/or the cutting member 34 and the second jaw body 44 to electrosurgically effect the anatomical feature. That is, once the anatomical feature is clamped between the jaws 20, 22, the anatomical feature can be electrically coagulated in the first use state by funning a voltage potential between the first jaw body 30 and/or the cutting member 34 and the second jaw body 44 so that the first therapy current flows from the first jaw body 30 and/or the cutting member 34 to the second jaw body 44, or vice versa, and through the anatomical feature thereby electrically coagulating the anatomical feature. In and during the first use state, a gap G' may be defined between the medial edge 38 of the cutting member 34 and the and 46. Alternatively, the anatomical feature can be non-electrically grasped and clamped between the effecting surface 52 of the cutting member 34 and the effecting surface 70 of the second jaw body 44 without passing a therapy current between any of the jaws 20, 22 or cutting member 34.

With continued reference to FIG. 2, the medical device 10 is operable or can be used in a second use state. In the second use state, the first jaw 20 and/or the second jaw body 22 can be repositioned so that the anatomical feature is positioned or sandwiched between the jaws 20, 22 and between the medial edge 38 of the cutting member 34 and an opposing medial edge 47 of the anvil 46. This can be achieved by moving the first jaw 20 generally in direction 60 and/or the second jaw 22 generally along direction 62 until the medial edge 38 of the cutting member 34 contacts the anatomical feature such that the jaw assembly 14 is in a closed position. This may be done before, after, or without moving the jaws 20, 22 in directions 56, 58 as was just previously discussed. The gap G' previously defined between the medial edge 38 of the cutting member 34 and the anvil 46 in the first use state is taken up when the jaw assembly 14 is in the closed position in the second use state.

The medical device 10 is configured to pass the second therapy current supplied by the poles 50a, 50b of the power source 24 between cutting member 34 and the first jaw body 30 the second jaw body 44, or both the first jaw body 30 and the second jaw body 44 and through the anatomical feature to electrically cut the anatomical feature. More precisely, the anatomical feature can be electrically cut in the second use state by contacting the anatomical feature with the medial edge 36 of the cutting member 34 while the anatomical feature is in contact with the anvil 46 and while passing the second therapy current between the cutting member 34 and either or both of the first jaw body 40 and the second jaw body 44. Alternatively, the anatomical feature can be non-electrically or mechanically cut in the second use state by moving the cut blade 38 against the medial edge 47 of anvil 46 with the anatomical feature therebetween without passing a therapy current (i.e., a cold cut blade).

With continued reference to FIG. 2, the first jaw 20 and/or the second jaw 22 may include one or more standoffs 76. The standoffs 76 may be insulators that function to prevent electrical shorting during electrical coagulation and/or electrical cutting by preventing the jaw bodies 30, 44 and/or the cutting member 34 from contacting each other when the jaw bodies 30, 44 and/or cutting member 34 are electrically charged and moved towards one another. It should also be noted that the medial edge 38 of the cutting member 34 contacting the anvil 46 may also function as a standoff to prevent the jaw bodies 30, 44 and/or cutting member 34 from contacting each other when one or both of the jaw bodies 30, 44 and cutting member 34 are electrically charged and moved towards each other.

Figure 3:
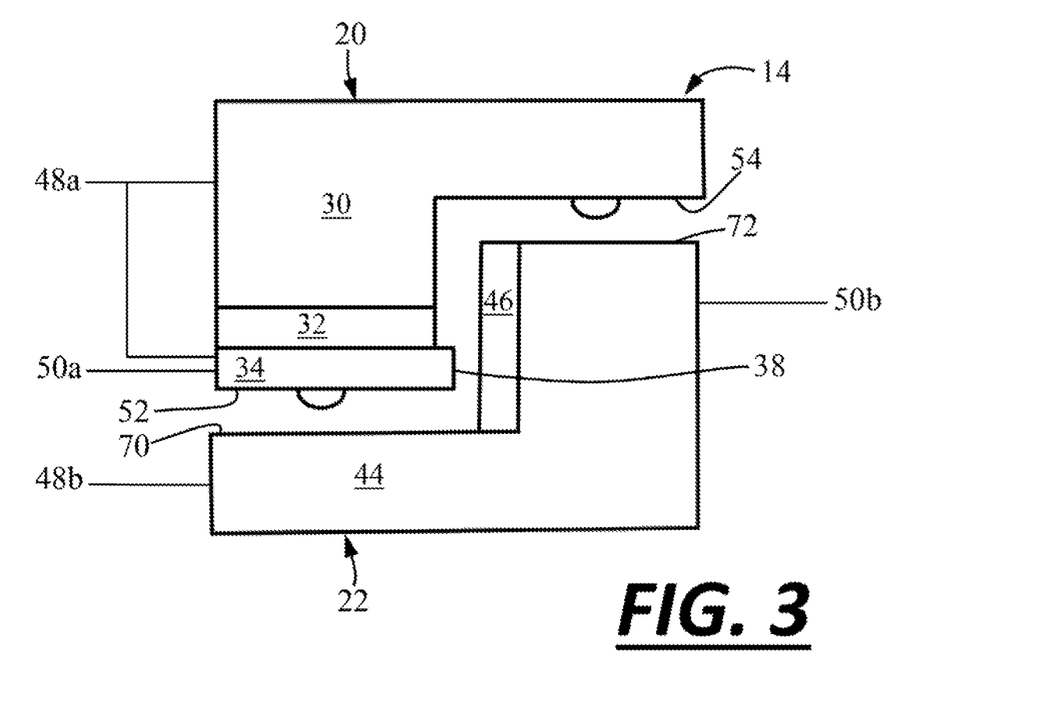
FIG. 3 is a cross-sectional view of the jaw assembly.

FIG. 3 illustrates a cross section of the jaw assembly 14. The jaw assembly 14 of FIG. 3 is substantially similar to the jaw assembly 14 illustrated and described in FIG. 2; therefore, many of the similar features of FIG. 3 will not be described again.

With continued reference to FIG. 3, both the first jaw body 30 and the cutting member 34 are in electrical communication with a first pole 48a of the power source 24 (FIG. 1). The second jaw body 44 is in electrical communication with a second pole 48b of the power source 24. A first therapy current is supplied from the poles 48a, 48b of the power supply 24 to the first jaw body 30, the second jaw body 44, and the cutting member 34.

With continued reference to FIG. 3, the cutting member 34 is also in electrical communication with another first pole 50a of the power source 24 (FIG. 1). Only the second jaw body 44 is in electrical communication with another second pole 50b of the power source 24. A second therapy current is supplied from the poles 50a, 50b of the power supply 24 to the first jaw body 30, the second jaw body 44, and the cutting member 34.

With continued reference to FIG. 3, the medical device 10 is operable or can be used in a first use state. In the first use state, an anatomical feature (not illustrated) is positioned between the first jaw 20 and the second jaw 22. More precisely, the anatomical feature can be positioned and/or clamped between an effecting surface 52 of the cutting member 34 and the opposing effecting surface 70 of the second jaw body 30 and/or between an effecting surface 54 of the first jaw body 30 and the opposing effecting surface 72 of the second jaw body 44. The anatomical feature can be captured, sandwiched, and/or clamped therebetween by moving the first jaw 20 towards the second jaw 22 generally in direction 56, and/or moving the second jaw 22 towards the first jaw 20 generally in direction 58 (See directions at FIG. 1) so that the jaw assembly 14 is in the closed position.

The medical device 10 is configured to pass the first therapy current supplied by the poles 48a, 48b of the power source 24 between the first jaw body 30 and/or the cutting member 34 and the second jaw body 44 to electrosurgically effect the anatomical feature. That is, once the anatomical feature is clamped between the jaws 20, 22, the anatomical feature can be electrically sealed or coagulated in the first use state by forming a voltage potential between the first jaw body 30 and/or the cutting member 34 and the second jaw body 44 so that the first therapy current flows from the first jaw body 30 and/or the cutting member 34 to the second jaw body 44, or vice versa, and through the anatomical feature thereby electrically coagulating the anatomical feature. In and during the first use state, a gap G' is defined between the medial edge 38 of the cutting member 32 and the anvil 46. Alternatively, the anatomical feature can be non-electrically grasped and clamped between the surfaces 52, 70 and/or surfaces 54 and 72 without passing a therapy current between any of the jaws 20, 22 or cutting member.

With continued reference to FIG. 3, the medical device 10 is operable or can be used in a second use state. In the second use state, the first jaw 20 and/or the second jaw 22 can be repositioned so that the anatomical feature is positioned or sandwiched between the jaws 20, 22 and between the medial edge 38 of the cutting member 32 and an opposing medial edge 47 of anvil 46. This can be achieved by moving the first jaw 20 generally in direction 60 and/or the second jaw 22 generally along direction 62 until the medial edge 38 of the cutting member 34 contacts the anatomical feature (See directions at FIG. 1) such that the jaw assembly 14 is moved into a closed position. This may be done before, after, or without moving the jaws 20, 22 in directions 56, 58 as was just previously discussed.

The medical device 10 is configured to pass the second therapy current supplied by the poles 50a, 50b of the power source 24 between cutting member 34 and the second jaw body 30 and through the anatomical feature to electrically cut the anatomical feature. More precisely, the anatomical feature can be electrically cut in the second use state by contacting the anatomical feature with the medial edge 38 of the cutting member 34 while passing the second therapy current between the cutting member 34 and the second jaw body 44. Alternatively, the anatomical feature can be non-electrically or mechanically cut in the second use state by moving the cut blade 38 against the medial edge 47 of the anvil 46 with the anatomical feature therebetween without passing a therapy current (i.e., a cold cut blade).

Figure 4:
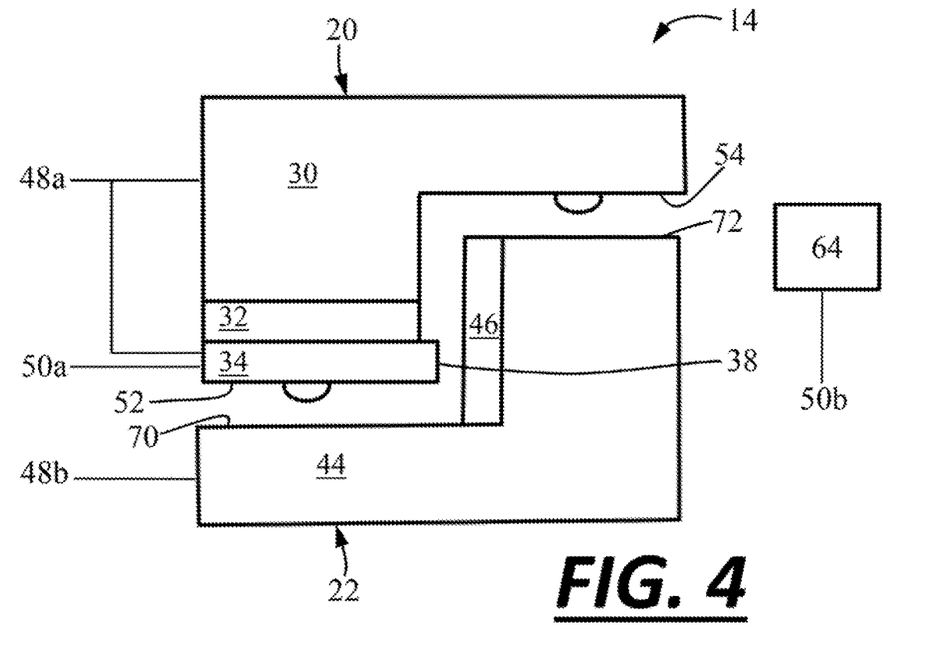
FIG. 4 is a cross-sectional view of the jaw assembly.

FIG. 4 illustrates a cross section of the jaw assembly 14. The jaw assembly 14 of FIG. 4 is substantially similar to the jaw assembly 14 illustrated and described in FIGS. 2 and 3; therefore, many of the similar features of FIG. 4 will not be described again.

With continued reference to FIG. 4 both the first jaw body 30 and the cutting member 34 are in electrical communication with a first pole 48a of the power source 24 (FIG. 1). The second jaw body 44 is in electrical communication with a second pole 48b of the power source 24. A first therapy current is supplied from the poles 48a, 48b of the power supply 24 to the first jaw body 30, the second jaw body 44, and the cutting member 34.

With continued reference to FIG. 4, the cutting member 34 is also in electrical communication with another first pole 50a of the power source 24 (FIG. 1). A remote electrode 64 is in communication with the second pole 50b of the power source 24. A second therapy current is passed between the poles 50a, 50b of the power supply 24 and between the cutting member 34 and the remote electrode 64.

With continued reference to FIG. 4, the medical device 10 is operable or can be used in a first use state. In the first use state, an anatomical feature (not illustrated) is positioned between the first jaw 20 and the second jaw 22. More precisely, the anatomical feature can be positioned and/or clamped between a surface 52 of the cutting member 34 and the opposing effecting surface 70 of the second jaw body 44 and/or between a surface 54 of the first jaw body 30 and the effecting surface 72 of the second jaw body 44. The anatomical feature can be captured, sandwiched, and/or clamped therebetween by moving the first jaw 20 towards the second jaw 22 generally in direction 56, and/or moving the second jaw 22 towards the first jaw 20 generally in direction 58 (See directions at FIG. 1) thus moving the jaw assembly 14 into a closed position.

The medical device 10 is configured to pass the first therapy current supplied by the poles 48a, 48b of the power source 24 between the first jaw body 30 and/or the cutting member 34 and the second jaw body 44 to electrosurgically effect the anatomical feature. That is, once the anatomical feature is clamped between the jaws 20, 22, the anatomical feature can be electrically coagulated in the first use state by forming a voltage potential between the first jaw body 30 and/or the cutting member 34 and the second jaw body 44 so that the first therapy current flows from the first jaw body 30 and/or the cutting member 34 to the second jaw body 44, or vice versa, and through the anatomical feature thereby electrically coagulating the anatomical feature. In and during the first use state, a gap G' is defined between the medial edge 38 of the cutting member 34 and the anvil 46. Alternatively, the anatomical feature can be non-electrically grasped and clamped between the surfaces 52, 70 and/or 54, 72 without passing a therapy current between any of the jaws 20, 22 or cutting member 34.

With continued reference to FIG. 4, the medical device 10 is operable or can be used in a second use state. In the second use state, the first jaw 20 and/or the second jaw 22 can be repositioned so that the anatomical feature is positioned or sandwiched between the jaws 20, 22 and between the medial edge 38 of the cutting member 34 and an opposing medial edge 47 of anvil 46. This can be achieved by moving the first jaw 20 generally in direction 60 and/or the second jaw 22 generally along direction 62 until the medial edge 38 of the cutting member 34 contacts the anatomical feature (See directions at FIG. 1) such that the jaw assembly 14 is in the closed position. This may be done before, after, or without moving the jaws 20, 22 in directions 56, 58 as was just previously discussed.

The medical device 10 is configured to pass the second therapy current supplied by the poles 50a, 50b of the power source 24 between cutting member 34 and the remote electrode 64 and through the anatomical feature to electrically cut the anatomical feature. More precisely, the anatomical feature can be electrically cut in the second use state by contacting the anatomical feature with the medial edge 38 of the cutting member 34 while passing the second therapy current between the cutting member 34 and the remote electrode 64. Alternatively, the anatomical feature can be non-electrically or mechanically cut in the second use state by moving the cut blade 38 against the medial edge of the anvil 46 with the anatomical feature therebetween without passing a therapy current (i.e., a cold cut blade).

Figure 5:
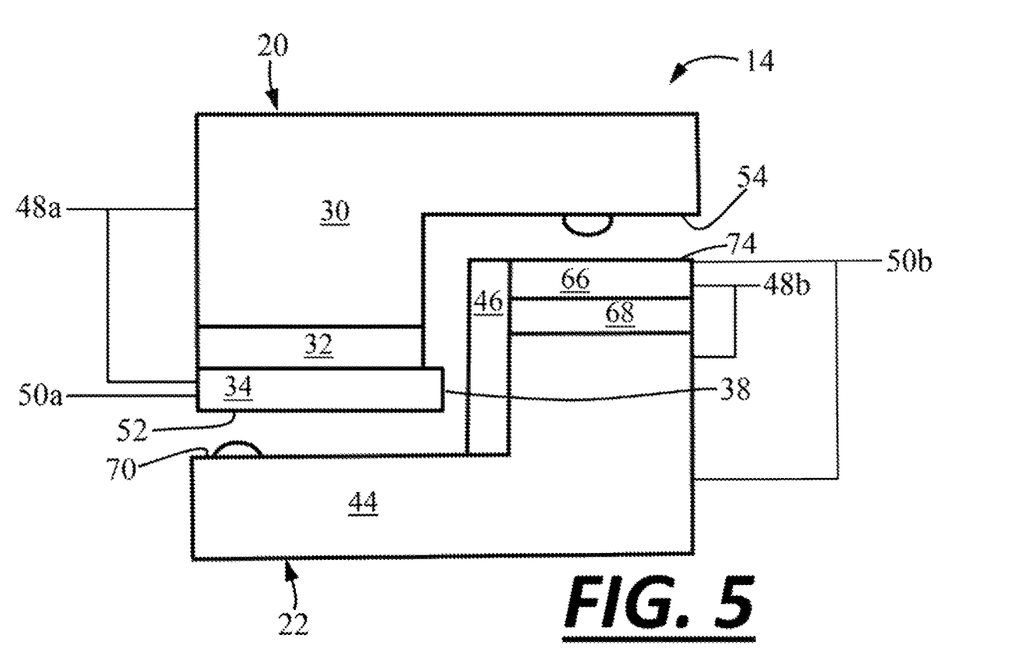
FIG. 5 is a cross-sectional view of the jaw assembly.

FIG. 5 illustrates a cross section of the jaw assembly 14. The jaw assembly 14 of FIG. 3 is substantially similar to the jaw assembly 14 illustrated and described in FIG. 2; therefore, many of the like features of FIG. 3 will not be described again.

With continued reference to FIG. 5, the second jaw 22 includes an electrode 66 and an insulator 68 between the electrode 66 and the second jaw body 44. Both the first jaw body 30 and the cutting member 34 are in electrical communication with a first pole 48a of the power source 24 (FIG. 1). Both the second jaw body 44 and the electrode 66 are in electrical communication with a second pole 48b of the power source 24. A first therapy current is supplied from the poles 48a, 48b of the power supply 24 to the first jaw body 30, the cutting member 34, the electrode 66, and the second jaw body 44.

With continued reference to FIG. 5, the cutting member 34 is also in electrical communication with another first pole 50a of the power source 24 (FIG. 1). Both the second jaw body 44 and the electrode 66 are in electrical communication with another second pole 50b of the power source 24. A second therapy current is supplied from the poles 50a, 50b of the power supply 24 to the culling member 34, the electrode 66, and the second jaw body 44.

With continued reference to FIG. 5, the medical device 10 is operable or can be used in a first use state. In the first use state, an anatomical feature (not illustrated) is positioned between the first jaw 20 and the second jaw 22. More precisely, the anatomical feature can be positioned and/or clamped between a surface 52 of the cutting member 34 and the opposing effecting surface 70 of the second jaw body 44 and/or between a surface 54 of the first jaw body 30 and the effecting opposing surface 74 of the electrode 66. The anatomical feature can be captured, sandwiched, and/or clamped therebetween by moving the first jaw 20 towards the second jaw 22 generally in direction 56, and or moving the second jaw 22 towards the first jaw 20 generally in direction 58 (See directions at FIG. 1) so that the jaw assembly 14 is moved into a closed position.

The medical device 10 is configured to pass the first therapy current supplied by the poles 48a, 48b of the power source 24 between the first jaw body 30, the electrode 66, and the second jaw body 44 to electrosurgically effect the anatomical feature. That is, once the anatomical feature is clamped between the jaws 20, 22, the anatomical feature can be electrically coagulated in the first use state by forming a voltage potential between the first jaw body 30 and/or the cutting member 34 and the electrode 66 and/or the second jaw body 44 so that the first therapy current flows from the first jaw body 30 and/or the cutting member 34 to the electrode 66 and/or to second jaw body 44, or vice versa, and through the anatomical feature thereby electrically coagulating the anatomical feature. In and during the first use state, a gap G' is defined between the medial edge 38 of the cutting member 34 and the anvil 46. Alternatively, the anatomical feature can be non-electrically grasped and clamped between the jaws 20, 22, without passing a therapy current between any of the jaws 20, 22 or cutting member.

With continued reference to FIG. 5, the medical device 10 is operable or can be used in a second use state. In the second use state, the first jaw 20 and/or the second jaw 22 can be repositioned so that the anatomical feature is positioned or sandwiched between the jaws 20, 22 and between the medial edge 38 of the cutting member 34 a medial edge 47 of the anvil 46. This can be achieved by moving the first jaw 20 generally in direction 60 and/or the second jaw 22 generally along direction 62 until the medial edge 38 of the cutting member 34 contacts the anatomical feature (See directions at FIG. 1) so that the jaw assembly 14 is moved into a closed position. This may be done before, after, or without moving the jaws 20 22 in directions 56, 58 as was just previously discussed.

The medical device 10 is configured to pass the second therapy current supplied by the poles 50*a*, 50*b* of the power source 24 between cutting member 34 and either or both of the electrode 66 and the second jaw body 44. More precisely, the anatomical feature can be electrically cut in the second use state by contacting the anatomical feature with the medial edge 38 of the cutting member 34 while forming a voltage potential between the cutting member 34 and the electrode 66 and/or the second jaw body 44 or both so that the second therapy current flows therebetween and through the anatomical feature thereby electrically coagulating the anatomical feature. Alternatively, the anatomical feature can be non-electrically or mechanically cut in the second use state by moving the cut blade 38 against the medial edge 47 of the anvil 46 with the anatomical feature therebetween without passing a therapy current (i.e., a cold cut blade).

FIG. 6 illustrates a cross section of the jaw assembly 14. The jaw assembly 14 includes a first jaw 20 and a second jaw 22 that are disposed in opposition relation relative to one another. The first jaw 20 includes a first jaw body 30 that may be configured as a cutting member 34. The second jaw 22 includes a first jaw body 44 that may be configured as an anvil 46.

With continued reference to FIG. 6, the medical device 10 is operable or can be used in a first use state. In the first use state, an anatomical feature (not illustrated) is positioned between the first jaw 20 and the second jaw 22. More precisely, the anatomical feature can be positioned and/or clamped between an effecting surface 52 of the cutting member 34 and an opposing effecting surface 70 of the second jaw body 30 and/or between effecting surface 54 of the first jaw body 30 and the opposing effecting surface 72 of the second jaw body 44. The effecting surface 72 is stepped off from the effecting surface 70, or vice versa. The anatomical feature can be captured, sandwiched, and/or clamped therebetween by moving the first jaw 20 towards the second jaw 22 generally in direction 56, and/or moving the second jaw 22 towards the first jaw 20 generally in direction 58 (See directions at FIG. 1) so that the jaw assembly 14 is moved into a closed position.

Each of the jaw bodies 30, 44 can be in communication with an opposing pole of the power source 24 (FIG. 1). The medical device 10 is operable or can be used in a first use state. The medical device 10 can be configured to pass a therapy current supplied by the opposing poles of the power source 24 between the first jaw body 30 and the second jaw body 44 to electrosurgically effect the anatomical feature. That is, once the anatomical feature is clamped between the jaws 20, 22, the anatomical feature can be electrically coagulated in the first use state by forming a voltage potential between the first jaw body 30 and the second jaw body 44 so that the first therapy current flows from the first jaw body 30 to the second jaw body 44, or vice versa, and through the anatomical feature thereby electrically coagulating the anatomical feature. Alternatively, the anatomical feature can be grasped or clamped between the jaw bodies 30, 44 without passing a therapy current therebetween. In and during the first use state, a gap G' is defined between the medial edge 38 of the cutting member 32 and the medial edge 47 of the anvil 46 or second jaw. This gap G' may be a lateral gap defined between the medial edges 38, 47 when the jaw assembly is in the closed position in the tint use state.

With continued reference to FIG. 6, the medical device 10 is operable or can be used in a second use state. In the second use state, the first jaw 20 and/or the second jaw 22 can be repositioned so that the anatomical feature is positioned or sandwiched between the jaws 20, 22 and between the medial edge 38 of the cutting member 32 and the medial edge 47 of the second jaw 22 or anvil 46. When the jaw assembly 14 is in both the open position and the closed position, the medial edge 38 of the cutting member 32 is in opposition to the medial edge 47 of the second jaw 22. This can be achieved by moving the first jaw 20 laterally or generally in direction 60 (i.e., lateral movement) and or the second jaw 22 laterally or generally along direction 62 (i.e., lateral Movement) until the medial edge 38 of the cutting member 34 contacts the anatomical feature (See directions at FIG. 1) so that the jaw assembly 14 is moved into a closed position. The medical device 10 can be configured to pass a second therapy current supplied by the opposing pole of the power source 24 between first jaw body 30 and the second jaw body 30 and through the anatomical feature to electrically cut the anatomical feature. More precisely, the anatomical feature can be electrically cut by contacting the anatomical feature with the medial edge 36 of the cutting member 34 while passing the second therapy current between the first jaw body 30 or the cutting member 34 and the second jaw body 44. Alternatively, the anatomical feature can be non-electrically or mechanically cut in the second use state by moving the cutting member 34 against the medial edge 47 of the anvil 46 with the anatomical feature therebetween without passing a therapy current (i.e., a cold cut blade).

The medial edge 38 of the cutting member 32 is disposed longitudinally on the effecting surface 52. The medial edge 47 of the second jaw 22 or anvil 46 is generally planar. The medial edge 47 of the second jaw 22 or anvil 46 is arranged generally or to both the effecting surface 70 of the second jaw 22 and the second effecting surface 72 of the second jaw 22. The effecting surface 70 of the second jaw 22 and the effecting surface 72 of the second jaw are both generally planar.

Figure 7:
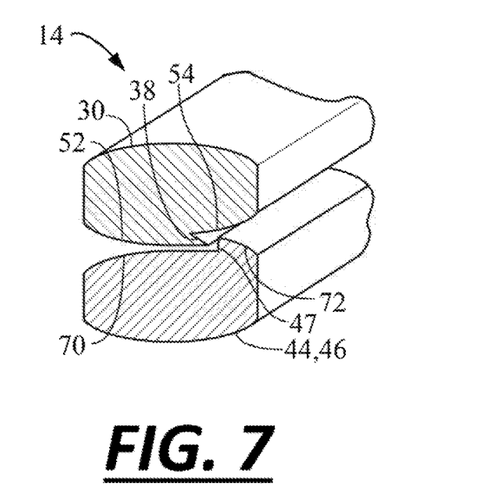
FIG. 7 is a cross-sectional view of the jaw assembly.

FIG. 7 illustrates a cross section of the jaw assembly 14. The jaw assembly 14 of FIG. 7 is substantially similar to the jaw assembly 14 illustrated and described in FIG. 6; therefore, many of the like features of FIG. 7 will not be described again.

In FIG. 7, the effecting surfaces 52 and 54 of the first jaw both 30 are generally curved, whereas these surfaces in FIG. 6 are generally planar. Similarly, the surfaces 70 and 72 of the second jaw body 44 are generally curved, whereas these surfaces in FIG. 6 are generally planar, A particular benefit of these curved surfaces on the first jaw body 30 and the second jaw body 44 is that they provide an increase force to thin the anatomical feature near the center of the jaw assembly 14 (i.e., axis 36; FIG. 2).

Figure 8:
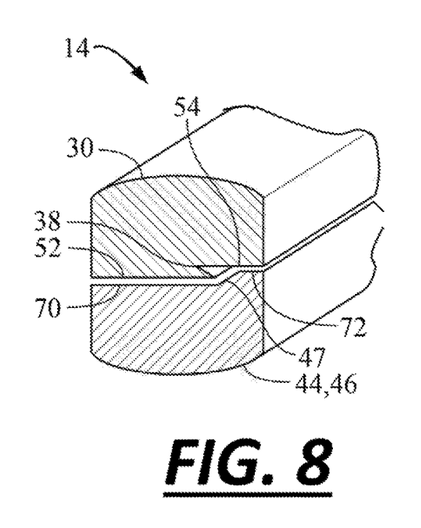
FIG. 8 is a cross-sectional view of the jaw assembly.

FIG. 8 illustrates a cross section of the jaw assembly 14. The jaw assembly 14 of FIG. 8 is substantially similar to the jaw assembly 14 illustrated and described in FIG. 6; therefore, many of the like features of FIG. 8 will not be described again.

In FIG. 8, the medial edge 47 of the 46 is angled relative to surfaces 54, 52, 70, 72 and relative to axis 36 (FIG. 2), while the medial edge 47 of the anvil 46 illustrated in FIG. 6 is generally orthogonal to these aforementioned surfaces.

Figure 9:
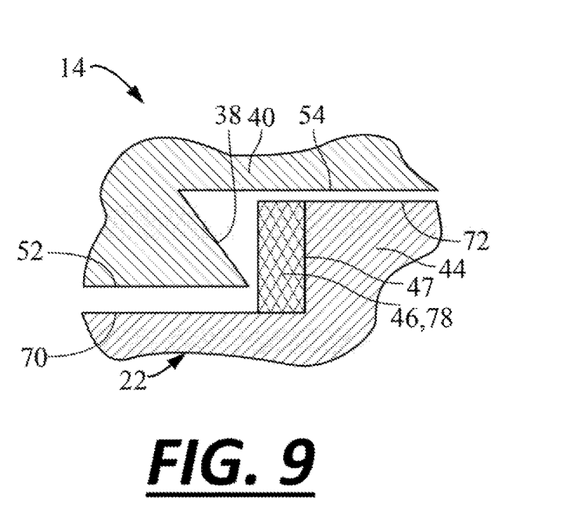
FIG. 9 is a cross-sectional view of the jaw assembly.

FIG. 9 illustrates a cross section of the jaw assembly 14. The jaw assembly 14 of FIG. 9 is substantially similar to the jaw assembly 14 illustrated and described in FIG. 6; therefore, many of the like features of FIG. 9 will not be described again.

In FIG. 9, the anvil 46 of the second jaw 22 comprises an elastic member or insulator 78. The elastic member or insulator 78 is positioned on the medial edge 47 of the second jaw 22 and between the medial edge 38 of the first jaw 20 and the medial edge 47 of the second jaw 22. The elastic member or insulator 78 is also positioned on the effecting surface 70 of the second jaw body 22. When the jaw assembly 14 is in the closed position, the medial edge of the first jaw is in opposition to the elastic member.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The disclosures of all articles and references, including patent applications and publications, are incorporated by reference for all purposes. Plural elements or steps can be provided by a single integrated element or step. Alternatively, a single element or step might be divided into separate plural elements or steps. The disclosure of "a" or "one" to describe an element or step is not intended to foreclose additional elements or steps. Moreover, it is understood that any feature(s) from a figure can removed from that figure and/or added to another figure. Similarly, one or more features in the above description can be added or removed from one or more of the figures illustrated in the drawings.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did riot consider such subject matter to be part of the disclosed inventive subject matter.

The invention claimed is:

1. An electrosurgical medical device for electrosurgically effecting an anatomical feature comprising: a jaw assembly comprising: a first jaw comprising a first jaw body and a cutting member; and a second jaw comprising a second jaw body, at least one of the first jaw body and the second jaw body vertically movable relative to the other of the first jaw body and the second jaw body between an open position and a closed position for grasping the anatomical feature, the jaw assembly configured such that in the closed position, a lateral gap is defined between a medial edge of the cutting member and a medial edge of the second jaw, and lateral movement of the first jaw body or the second jaw body closes the lateral gap to cut the anatomical feature; wherein during a first use state, the medical device is configured to pass a therapy current supplied by a power source between the first jaw body and the second jaw body to electrosurgically effect the anatomical feature, and wherein during a second use state, the anatomical feature is configured to be electrosurgically effected by contacting the anatomical feature with the medial edge of the cutting member while a second therapy current from the power source is passed between the cutting member and the first jaw body and/or the second jaw body.

2. The electrosurgical medical device of claim 1, wherein the cutting member includes an exterior edge and an interior edge, the medial edge is the interior edge.

3. The electrosurgical medical device of claim 1, wherein the second jaw comprises an electrode, and
   wherein during the second use state, the second therapy current is passed between the cutting member and the second jaw body, the electrode, or both the second jaw body and the electrode.

4. The electrosurgical medical device of claim 1, wherein the second jaw comprises an anvil that is an insulator, and during the second use state the anatomical feature is configured to be sandwiched between and in contact with both the cutting member and the anvil.

5. The electrosurgical medical device of claim 1, wherein the first jaw body and the cutting member are in contact with a first pole of the power source, and the second jaw body is in contact with a second pole of the power source, wherein an insulator is located between the first jaw body and the cutting member.

6. The electrosurgical medical device of claim 1, wherein an insulator is located between the first jaw body and the cutting member and the medial edge of the cutting member extends medially beyond a medial edge of the insulator.

7. The electrosurgical medical device of claim 1, wherein during the first use state, the anatomical feature is clamped and/or coagulated, and
   wherein the anatomical feature is cut during the second use state.

8. The electrosurgical medical device of claim 1, wherein at least one of the cutting member, the first jaw body, and the second jaw body includes a standoff, the standoff prevents the cutting member from contacting the second jaw body and/or the first jaw body from contacting the second jaw body.

9. A medical device for electrosurgically effecting an anatomical feature comprising: a jaw assembly comprising: a first jaw comprising a cutting member; and a second jaw comprising an anvil; wherein the medical device is operable in a first use state and in a second use state, wherein during the first use state, a lateral gap is defined between an interior edge of the cutting member and the anvil while the first jaw and/or the second jaw move vertically along a first path relative to each other to clamp the anatomical feature between the cutting member and the second jaw, and wherein during the second use state, the lateral gap is reduced while the first jaw and/or the second jaw move laterally along a second path relative to each other to cut the anatomical feature with the interior edge of the cutting member.

10. The medical device of claim 9, wherein the first jaw comprises a first jaw body and the second jaw comprises a second jaw body,
   wherein during the first use state, the medical device is configured to pass a first therapy current supplied by a power source between the first jaw body and the second jaw body to coagulate the anatomical feature, and
   wherein during the second use state, the medical device is configured to pass a second therapy current supplied by the power source from the interior edge of the cutting member through the anatomical feature to electrosurgically cut the anatomical feature.

11. The medical device of claim 10, wherein the first jaw body and the cutting member are in contact with a first pole of the power source, and the second jaw body is in contact with a second pole of the power source,
   wherein an insulator is located between the first jaw body and the cutting member.

12. The medical device of claim 10, wherein an insulator is located between the first jaw body and the cutting member wherein the interior edge of the cutting member extends medially beyond an interior edge of the insulator.

13. The medical device of claim 10, wherein during the second use state, the second therapy current is passed from the cutting member to the first jaw body, or to the second jaw body, or to both the first jaw body and the second jaw body.

14. The medical device of claim 10, wherein the second jaw body comprises an electrode, and
   wherein in the second use state, the second therapy current is passed from the cutting member to the second jaw body, or to the electrode, or to both the second jaw body and the electrode.

15. The medical device of claim 10, wherein at least one of the cutting member, the first jaw body, and the second jaw body includes a standoff, the standoff prevents the cutting member from directly contacting the second jaw body and/or the first jaw body from directly contacting the second jaw body.

16. An electrosurgical medical device comprising:
   a jaw assembly comprising:
      a first jaw comprising a first jaw body and a cutting member; and
      a second jaw comprising a second jaw body and an anvil;
   wherein during a first use state, a lateral gap is defined between an interior edge of the cutting member and the anvil while the jaws move vertically between an open position and a closed position for grasping an anatomical feature, and
   wherein during a second use state, the lateral gap is reduced while the jaws move laterally between an open position and a closed position and the medical device is configured to pass a second use state therapy current from the cutting member through the anatomical feature to electrosurgically effect the anatomical feature in the second use state.

17. The electrosurgical medical device of claim 16, wherein an insulator is located between the first jaw body and the cutting member.

18. The electrosurgical medical device of claim 16, wherein at least one of the cutting member, the first jaw body, and the second jaw body includes a standoff, the standoff prevents the cutting member from contacting the second jaw body and/or the first jaw body from contacting the second jaw body.

19. The electrosurgical medical device of claim 16, wherein during the first use state, the anatomical feature is clamped and/or coagulated, and wherein the anatomical feature is cut during the second use state.

20. The electrosurgical medical device of claim 16, wherein the second jaw comprises an electrode.

* * * * *